United States Patent [19]

Iovanna et al.

[11] Patent Number: 5,959,086
[45] Date of Patent: Sep. 28, 1999

[54] ANTIBODIES SPECIFIC FOR HUMAN PANCREATITIS ASSOCIATED PROTEIN

[75] Inventors: Juan-Lucio Iovanna, Marseille, France; Volker Keim, Heddesheim, Germany; Jean-Charles Dagorn, Marseille, France

[73] Assignee: Institut National de la Santa et de la Recherche Medicale, Paris Cedex, France

[21] Appl. No.: 08/422,166

[22] Filed: Apr. 14, 1995

Related U.S. Application Data

[62] Division of application No. 07/778,156, filed as application No. PCT/FR91/00323, Apr. 18, 1991, Pat. No. 5,436,169.

[30] Foreign Application Priority Data

Apr. 20, 1990 [FR] France ................................. 90 05062

[51] Int. Cl.⁶ ........................ A61K 39/395; C07K 16/18; C12N 5/12; G01N 33/53
[52] U.S. Cl. .................................. 530/387.9; 424/139.1; 424/145.1; 424/152.1; 424/158.1; 424/9.1; 424/9.34; 435/7.1; 435/70.21; 435/331; 435/332; 435/336; 530/387.1; 530/388.1; 530/388.2; 530/388.24; 530/389.1; 530/389.2
[58] Field of Search ................................ 435/70.21, 7.1, 435/7.2, 172.2, 332, 336; 530/387.1, 388.2, 388.24; 424/130.1, 139.1, 158.1

[56] References Cited

U.S. PATENT DOCUMENTS 5,436,169  7/1995  Iovanna et al. .

OTHER PUBLICATIONS

Scaver S. Genetic Engineering News 14(14):10 and 21, Aug. 1994.
Keim, V. and Loffler H.G. Clinical Physiology and Biochemistry 4(2):136–142, 1986.
Keim, V. et al. Gastroenterology 103(1):248–254, 1992.
Goding, J.W. "Monoclonal Antibodies: Priciples and Practice" 2nd ed. Academic Press, New York, 1986.
Reeck, G.R. et al. Cell 50:667, Aug. 1987.

*Primary Examiner*—Christina Y. Chan
*Assistant Examiner*—Phillip Gambel
*Attorney, Agent, or Firm*—Oblon, Spivak, McClelland, Maier & Neustadt, P.C.

[57] ABSTRACT

The invention relates to the family of the protein (PAP) associated with acute pancreatitis in man and in the rat. It also relates to the nucleotide fragments coding for the above proteins. Also included in the framework of the invention are antibodies which recognize the PAP and which are capable of being used for the purpose of diagnosing pancreatitis. The invention also relates to the production of the PAP, in particular by genetic engineering.

14 Claims, 6 Drawing Sheets

PAP
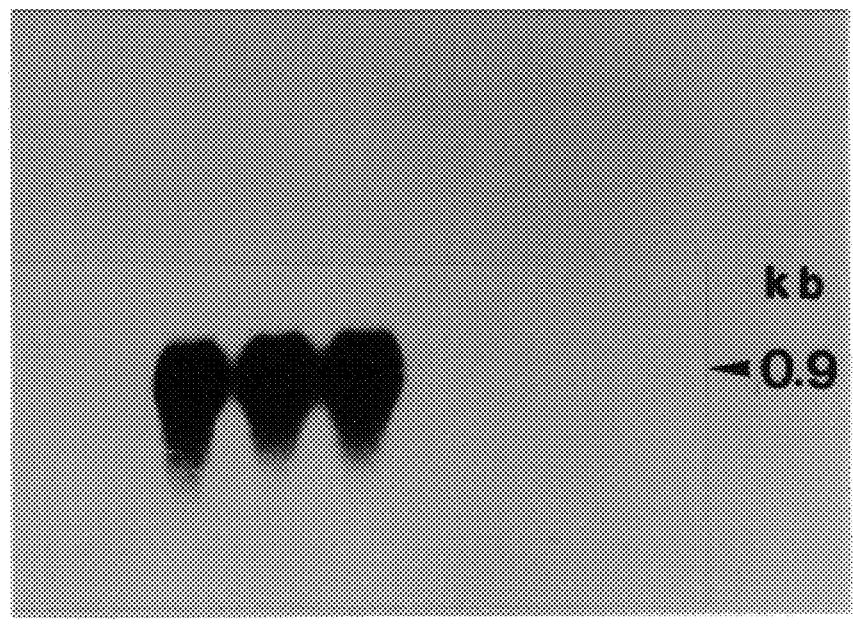
FIG.IA
AM
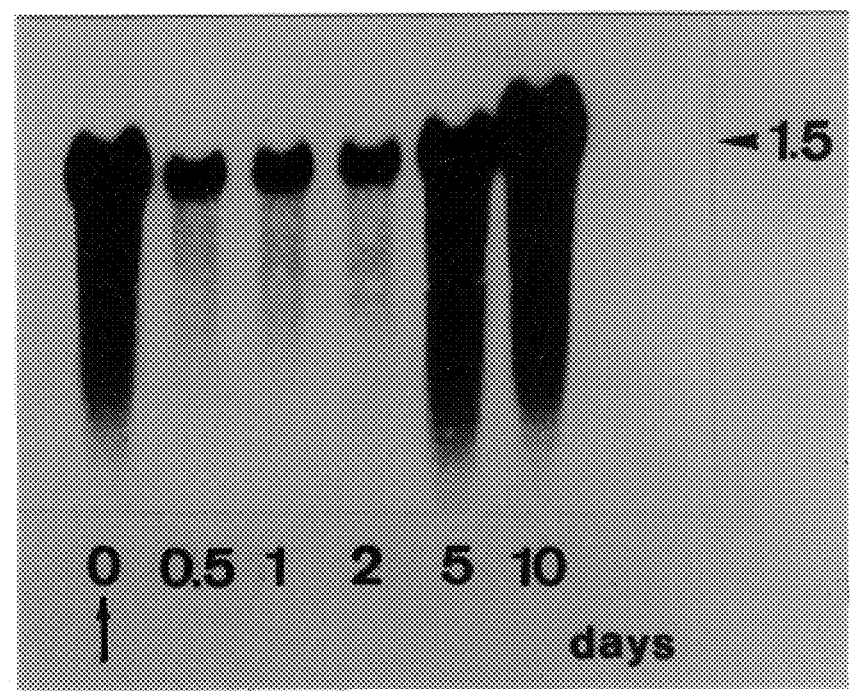
FIG.IB

```
AAAACCATCCAAATCGCCCGCAAGACAGCTAAGGAGGAGCAGAAAGATGATG    52

AGAGTTAAT ATG TTG CAT CGC TTG GCC TTC CCA GTC ATG        91
          Met Leu His Arg Leu Ala Phe Pro Val Met

TCC TGG ATG CTG CTC TCC TGC CTG ATG CTC TTA TCA CAG     130
Ser Trp Met Leu Leu Ser Cys Leu Met Leu Leu Ser Gln

GTG CAA GGA GAA GAC TCT CCG AAG AAA ATA CCC TCT GCA     169
Val Gln Gly Glu Asp Ser Pro Lys Lys Ile Pro Ser Ala

CGC ATT AGT TGC CCC AAA GGC TCC CAG GCA TAT GGC TCC     208
Arg Ile Ser Cys Pro Lys Gly Ser Gln Ala Tyr Gly Ser

TAC TGC TAT GCC CTG TTT CAG ATA CCA CAG ACC TGG TTT     247
Tyr Cys Tyr Ala Leu Phe Gln Ile Pro Gln Thr Trp Phe

GAT GCA GAA CTG GCC TGC CAG AAG AGA CCT GAA GGA CAC     286
Asp Ala Glu Leu Ala Cys Gln Lys Arg Pro Glu Gly His

CTT GTA TCT GTG CTC AAT GTA GCT GAA GCT TCA TTC TTG     325
Leu Val Ser Val Leu Asn Val Ala Glu Ala Ser Phe Leu

GCA TCC ATG GTC AAG AAC ACT GGA AAC AGC TAC CAA TAT     364
Ala Ser Met Val Lys Asn Thr Gly Asn Ser Tyr Gln Tyr

ACC TGG ATT GGA CTC CAT GAC CCC ACT CTT GGT GGA GAA     403
Thr Trp Ile Gly Leu His Asp Pro Thr Leu Gly Gly Glu

CCC AAT GGA GGT GGA TGG GAG TGG AGT AAC AAT GAC ATA     442
Pro Asn Gly Gly Gly Trp Glu Trp Ser Asn Asn Asp Ile

ATG AAT TAT GTC AAC TGG GAG AGG AAC CCA TCT ACT GCC     481
Met Asn Tyr Val Asn Trp Glu Arg Asn Pro Ser Thr Ala

TTA GAC CGC GGA TTC TGT GGC AGC TTG TCA AGA TCT TCT     520
Leu Asp Arg Gly Phe Cys Gly Ser Leu Ser Arg Ser Ser
```

FIG.2A

```
GGA TTT CTA AGA TGG AGA GAT ACC ACA TGT GAA GTT GAA   559
Gly Phe Leu Arg Trp Arg Asp Thr Thr Cys Glu Val Glu

GTT GCC CTA CGT CTG CAA ATT TAC AGG TTA AAA TTA CCA   598
Val Ala Leu Arg Leu Gln Ile Tyr Arg Leu Lys Leu Pro

GAC AGC AAA CAG CTT T AGTTTGTCCTGAAGCACATCCTGTCAAGGG  644
Asp Ser Lys Gln Leu

GCAAAATATGAAGACTTGCGTAGAAAAAGTGTATTCTATCTACAGTCCATAT  696

TGGAGCTCTAATCATTCTTTAGCCAATTTTGTATAAGTTGTGTCCTCATGTC  748

TTGGAAAGCAGTAATAAACCTCAGTCTCTCTTCGAAAAAAAAAAA         793
```

FIG.2B

| | |
|---|---|
| TTT GTT AAG GAT TCC CTT GAG AAT TAT GTA AAA GTT TTA | 39 |
| Phe Val Lys Asp Ser Leu Glu Asn Tyr Val Lys Val Leu | 13 |
| | |
| CAA GAG TCC ATC TCA TTC TCT TTG TCC CCC TCA AAG CTG | 78 |
| Gln Glu Ser Ile Ser Phe Ser Leu Ser Pro Ser Lys Leu | 26 |
| | |
| GCT TGC CAG AAG CGG CCC TCT GGA AAA CTG GTG TCT GTG | 117 |
| Ala Cys Gln Lys Arg Pro Ser Gly Lys Leu Val Ser Val | 39 |
| | |
| CTC AGT GGG GCT GAG GGA TCC TTC GTG TCC TCC CTG GTG | 156 |
| Leu Ser Gly Ala Glu Gly Ser Phe Val Ser Ser Leu Val | 52 |
| | |
| AGG AGC ATT AGT AAC AGC TAC TCA TAC ATC TGG ATT GGG | 195 |
| Arg Ser Ile Ser Asn Ser Tyr Ser Tyr Ile Trp Ile Gly | 65 |
| | |
| CTC CAT GAC CCC ACA CAG GTG CGA GTA TAT CCT CCC CTC | 234 |
| Leu His Asp Pro Thr Gln Val Arg Val Tyr Pro Pro Leu | 78 |
| | |
| TCT GTT ACC TCT CAA GGT ACT GTT GTT GCC CAG GCG CAC | 273 |
| Ser Val Thr Ser Gln Gly Thr Val Val Ala Gln Ala His | 91 |
| | |
| TCC CTG TCC CCA GTC CCT GCC CAG GAA GTA CTT | 306 |
| Ser Leu Ser Pro Val Pro Ala Gln Glu Val Leu | 102 |

FIG.3

|  |  |
|---|---|
| cggggagagtgactcctgattgcctcctcaagtcgcagacact ATG CTG | 48 |
| Met Leu | 2 |
| CCT CCC ATG GCC CTG CCC AGT GTA TCT TGG ATG CTG CTT | 87 |
| Pro Pro Met Ala Leu Pro Ser Val Ser Trp Met Leu Leu | 15 |
| TCC TGC CTC ATG CTG CTG TCT CAG GTT CAA GGT GAA GAA | 126 |
| Ser Cys Leu Met Leu Leu Ser Gln Val Gln Gly Glu Glu | 28 |
| CCC CAG AGG GAA CTG CCC TCT GCA CGG ATC CGC TGT CCC | 165 |
| Pro Gln Arg Glu Leu Pro Ser Ala Arg Ile Arg Cys Pro | 41 |
| AAA GGC TCC AAG GCC TAT GGC TCC CAC TGC TAT GCC TTG | 204 |
| Lys Gly Ser Lys Ala Tyr Gly Ser His Cys Tyr Ala Leu | 54 |
| TTT TTG TCA CCA AAA TCC TGG ACA GAT GCA GAT CTG GCC | 243 |
| Phe Leu Ser Pro Lys Ser Trp Thr Asp Ala Asp Leu Ala | 67 |
| TGC CAG AAG CGG CCC TCT GGA AAC CTG GTG TCT GTG CTC | 282 |
| Cys Gln Lys Arg Pro Ser Gly Asn Leu Val Ser Val Leu | 80 |
| AGT GGG GCT GAG GGA TCC TTC GTG TCC TCC CTG GTG AAG | 321 |
| Ser Gly Ala Glu Gly Ser Phe Val Ser Ser Leu Val Lys | 93 |
| AGC ATT GGT AAC AGC TAC TCA TAC GTC TGG ATT GGG CTC | 360 |
| Ser Ile Gly Asn Ser Tyr Ser Tyr Val Trp Ile Gly Leu | 106 |
| CAT GAC CCC ACA CAG GGC ACC GAG CCC AAT GGA GAA GGT | 399 |
| His Asp Pro Thr Gln Gly Thr Glu Pro Asn Gly Glu Gly | 119 |
| TGG GAG TGG AGT AGC AGT GAT GTG ATG AAT TAC TTT GCA | 438 |
| Trp Glu Trp Ser Ser Ser Asp Val Met Asn Tyr Phe Ala | 132 |
| TGG GAG AGA AAT CCC TCC ACC ATC TCA AGC CCC GGC CAC | 477 |
| Trp Glu Arg Asn Pro Ser Thr Ile Ser Ser Pro Gly His | 145 |
| TGT GCG AGC CTG TCC AGA AGC ACA GCA TTT CTG AGG TGG | 516 |
| Cys Ala Ser Leu Ser Arg Ser Thr Ala Phe Leu Arg Trp | 158 |

FIG.4A

```
AAA GAT TAT AAC TGT AAT GTG AGG TTA CCC TAT GTC TGC  555
Lys Asp Tyr Asn Cys Asn Val Arg Leu Pro Tyr Val Cys  171

AAA GTT CAC  tgactagtgcaggagggaagtcagcagcctgtgtttggt  603
Lys Val His                                          174 gtgcaactcatcatgggcatgagaccagtgtgaggactcaccctggaagaga  655 atattcgcttaattcccccaacctgaccacctcattcttatctttcttctgt  707 ttcttcctccccgctagtcatttcagtctcttcattttgtcatacggcctaa  759 ggctttaaagagcaataaaattttagtctgcaaaaaaa                798
```

FIG.4B

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 793 base pairs
        (B) TYPE: nucleic acid
        (C) STRANDEDNESS: unknown
        (D) TOPOLOGY: unknown (ii) MOLECULE TYPE: cDNA to mRNA (vi) ORIGINAL SOURCE:
        (A) ORGANISM: rat (F) TISSUE TYPE: pancreas (ix) FEATURE:
(A) NAME/KEY: CDS
(B) LOCATION: 62..613

(xi) SEQUENCE DESCRIPTION: SEQ ID NO:1:

```
AAAACCATCC AAATCGCCCG CAAGACAGCT AAGGAGGAGC AGAAAGATGA TGAGAGTTAA      60

T ATG TTG CAT CGC TTG GCC TTC CCA GTC ATG TCC TGG ATG CTG CTC         106
  Met Leu His Arg Leu Ala Phe Pro Val Met Ser Trp Met Leu Leu
   1               5                  10                  15

TCC TGC CTG ATG CTC TTA TCA CAG GTG CAA GGA GAA GAC TCT CCG AAG       154
Ser Cys Leu Met Leu Leu Ser Gln Val Gln Gly Glu Asp Ser Pro Lys
                 20                  25                  30

AAA ATA CCC TCT GCA CGC ATT AGT TGC CCC AAA GGC TCC CAG GCA TAT       202
Lys Ile Pro Ser Ala Arg Ile Ser Cys Pro Lys Gly Ser Gln Ala Tyr
                     35                  40                  45

GGC TCC TAC TGC TAT GCC CTG TTT CAG ATA CCA CAG ACC TGG TTT GAT       250
Gly Ser Tyr Cys Tyr Ala Leu Phe Gln Ile Pro Gln Thr Trp Phe Asp
             50                  55                  60

GCA GAA CTG GCC TGC CAG AAG AGA CCT GAA GGA CAC CTT GTA TCT GTG       298
Ala Glu Leu Ala Cys Gln Lys Arg Pro Glu Gly His Leu Val Ser Val
 65                  70                  75

CTC AAT GTA GCT GAA GCT TCA TTC TTG GCA TCC ATG GTC AAG AAC ACT       346
Leu Asn Val Ala Glu Ala Ser Phe Leu Ala Ser Met Val Lys Asn Thr
 80                  85                  90                  95

GGA AAC AGC TAC CAA TAT ACC TGG ATT GGA CTC CAT GAC CCC ACT CTT       394
Gly Asn Ser Tyr Gln Tyr Thr Trp Ile Gly Leu His Asp Pro Thr Leu
                    100                 105                 110

GGT GGA GAA CCC AAT GGA GGT GGA TGG GAG TGG AGT AAC AAT GAC ATA       442
Gly Gly Glu Pro Asn Gly Gly Gly Trp Glu Trp Ser Asn Asn Asp Ile
                115                 120                 125

ATG AAT TAT GTC AAC TGG GAG AGG AAC CCA TCT ACT GCC TTA GAC CGC       490
Met Asn Tyr Val Asn Trp Glu Arg Asn Pro Ser Thr Ala Leu Asp Arg
            130                 135                 140

GGA TTC TGT GGC AGC TTG TCA AGA TCT TCT GGA TTT CTA AGA TGG AGA       538
Gly Phe Cys Gly Ser Leu Ser Arg Ser Ser Gly Phe Leu Arg Trp Arg
145                 150                 155

GAT ACC ACA TGT GAA GTT GAA GTT GCC CTA CGT CTG CAA ATT TAC AGG       586
Asp Thr Thr Cys Glu Val Glu Val Ala Leu Arg Leu Gln Ile Tyr Arg
160                 165                 170                 175

TTA AAA TTA CCA GAC AGC AAA CAG CTT TAGTTTGTCC TGAAGCACAT             633
Leu Lys Leu Pro Asp Ser Lys Gln Leu
                180

CCTGTCAAGG GGCAAAATAT GAAGACTTGC GTAGAAAAAG TGTATTCTAT CTACAGTCCA     693

TATTGGAGCT CTAATCATTC TTTAGCCAAT TTTGTATAAG TTGTGTCCTC ATGTCTTGGA     753

AAGCAGTAAT AAACCTCAGT CTCTCTTCGA AAAAAAAAA                             793
```

(2) INFORMATION FOR SEQ ID NO:2:

(i) SEQUENCE CHARACTERISTICS:
(A) LENGTH: 184 amino acids
(B) TYPE: amino acid
(D) TOPOLOGY: linear (ii) MOLECULE TYPE: protein (xi) SEQUENCE DESCRIPTION: SEQ ID NO:2:

```
Met Leu His Arg Leu Ala Phe Pro Val Met Ser Trp Met Leu Leu Ser
 1               5                  10                  15

Cys Leu Met Leu Leu Ser Gln Val Gln Gly Glu Asp Ser Pro Lys Lys
```

```
                  20                  25                  30
Ile Pro Ser Ala Arg Ile Ser Cys Pro Lys Gly Ser Gln Ala Tyr Gly
            35                  40                  45

Ser Tyr Cys Tyr Ala Leu Phe Gln Ile Pro Gln Thr Trp Phe Asp Ala
 50                  55                  60

Glu Leu Ala Cys Gln Lys Arg Pro Glu Gly His Leu Val Ser Val Leu
 65                  70                  75                  80

Asn Val Ala Glu Ala Ser Phe Leu Ala Ser Met Val Lys Asn Thr Gly
                 85                  90                  95

Asn Ser Tyr Gln Tyr Thr Trp Ile Gly Leu His Asp Pro Thr Leu Gly
            100                 105                 110

Gly Glu Pro Asn Gly Gly Trp Glu Trp Ser Asn Asn Asp Ile Met
            115                 120                 125

Asn Tyr Val Asn Trp Glu Arg Asn Pro Ser Thr Ala Leu Asp Arg Gly
130                 135                 140

Phe Cys Gly Ser Leu Ser Arg Ser Ser Gly Phe Leu Arg Trp Arg Asp
145                 150                 155                 160

Thr Thr Cys Glu Val Glu Val Ala Leu Arg Leu Gln Ile Tyr Arg Leu
                165                 170                 175

Lys Leu Pro Asp Ser Lys Gln Leu
            180
```

(2) INFORMATION FOR SEQ ID NO:3:

(i) SEQUENCE CHARACTERISTICS:
        (A) LENGTH: 158 amino acids
        (B) TYPE: amino acid
        (D) TOPOLOGY: unknown (ii) MOLECULE TYPE: protein (vi) ORIGINAL SOURCE:
        (A) ORGANISM: Homo sapiens
        (F) TISSUE TYPE: pancreas (xi) SEQUENCE DESCRIPTION: SEQ ID NO:3:

```
Glu Asp Ser Pro Lys Lys Ile Pro Ser Ala Arg Ile Ser Cys Pro Lys
 1                   5                  10                  15

Gly Ser Gln Ala Tyr Gly Ser Tyr Cys Tyr Ala Leu Phe Gln Ile Pro
                20                  25                  30

Gln Thr Trp Phe Asp Ala Glu Leu Ala Cys Gln Lys Arg Pro Glu Gly
            35                  40                  45

His Leu Val Ser Val Leu Asn Val Ala Glu Ala Ser Phe Leu Ala Ser
 50                  55                  60

Met Val Lys Asn Thr Gly Asn Ser Tyr Gln Tyr Thr Trp Ile Gly Leu
 65                  70                  75                  80

His Asp Pro Thr Leu Gly Gly Glu Pro Asn Gly Gly Gly Trp Glu Trp
                 85                  90                  95

Ser Asn Asn Asp Ile Met Asn Tyr Val Asn Trp Glu Arg Asn Pro Ser
            100                 105                 110

Thr Ala Leu Asp Arg Gly Phe Cys Gly Ser Leu Ser Arg Ser Ser Gly
            115                 120                 125

Phe Leu Arg Trp Arg Asp Thr Thr Cys Glu Val Glu Val Ala Leu Arg
            130                 135                 140

Leu Gln Ile Tyr Arg Leu Lys Leu Pro Asp Ser Lys Gln Leu
145                 150                 155
```

(2) INFORMATION FOR SEQ ID NO:4:

(i) SEQUENCE CHARACTERISTICS:
    (A) LENGTH: 522 base pairs
    (B) TYPE: nucleic acid
    (C) STRANDEDNESS: unknown
    (D) TOPOLOGY: unknown (ii) MOLECULE TYPE: cDNA (vi) ORIGINAL SOURCE:
    (A) ORGANISM: Homo sapiens
    (F) TISSUE TYPE: pancreas (xi) SEQUENCE DESCRIPTION: SEQ ID NO:4:

```
ATGCTGCCTC CCATGGCCCT GCCCAGTGTA TCTTGGATGC TGCTTTCCTG CCTCATGCTG        60

CTGTCTCAGG TTCAAGGTGA AGAACCCCAG AGGGAACTGC CCTCTGCACG GATCCGCTGT       120

CCCAAAGGCT CCAAGGCCTA TGGCTCCCAC TGCTATGCCT TGTTTTTGTC ACCAAAATCC       180

TGGACAGATG CAGATCTGGC CTGCCAGAAG CGGCCCTCTG GAAACCTGGT GTCTGTGCTC       240

AGTGGGGCTG AGGGATCCTT CGTGTCCTCC CTGGTGAAGA GCATTGGTAA CAGCTACTCA       300

TACGTCTGGA TTGGGCTCCA TGACCCCACA CAGGGCACCG AGCCCAATGG AGAAGGTTGG       360

GAGTGGAGTA GCAGTGATGT GATGAATTAC TTTGCATGGG AGAGAAATCC CTCCACCATC       420

TCAAGCCCCG GCCACTGTGC GAGCCTGTCG AGAAGCACAG CATTTCTGAG GTGGAAAGAT       480

TATAACTGTA ATGTGAGGTT ACCCTATGTC TGCAAAGTTC AC                         522
```

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens
        (D) DEVELOPMENTAL STAGE: pancreas (xi) SEQUENCE DESCRIPTION: SEQ ID NO:5:

```
CGGGAGAGTG ACTCCTGATT GCCTCCTCAA GTCGCAGACA CT                          42
```

(2) INFORMATION FOR SEQ ID NO:6:

(i) SEQUENCE CHARACTERISTICS:
        (A) LENGTH: 234 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens
        (F) TISSUE TYPE: pancreas (xi) SEQUENCE DESCRIPTION: SEQ ID NO:6:

```
TGACTAGTGC AGGAGGGAAG TCAGCAGCCT GTGTTTGGTG TGCAACTCAT CATGGGCATG        60

AGACCAGTGT GAGGACTCAC CCTGGAAGAG AATATTCGCT TAATTCCCCC AACCTGACCA       120

CCTCATTCTT ATCTTTCTTC TGTTTCTTCC TCCCCGCTAG TCATTTCAGT CTCTTCATTT       180

TGTCATACGG CCTAAGGCTT TAAAGAGCAA TAAAATTTTT AGTCTGCAAA AAAA            234
```

(2) INFORMATION FOR SEQ ID NO:7:

(i) SEQUENCE CHARACTERISTICS:
        (A) LENGTH: 174 amino acids
        (B) TYPE: amino acid
        (D) TOPOLOGY: unknown (ii) MOLECULE TYPE: protein (vi) ORIGINAL SOURCE:
        (A) ORGANISM: Homo sapiens
        (F) TISSUE TYPE: pancreas (xi) SEQUENCE DESCRIPTION: SEQ ID NO:7:

Met Leu Pro Pro Met Ala Leu Pro Ser Val Ser Trp Met Leu Leu Ser
 1               5                  10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Val His
                165                 170

(2) INFORMATION FOR SEQ ID NO:8:

(i) SEQUENCE CHARACTERISTICS:
        (A) LENGTH: 474 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: rat
        (F) TISSUE TYPE: pancreas (xi) SEQUENCE DESCRIPTION: SEQ ID NO:8:

GAAGACTCTC CGAAGAAAAT ACCCTCTGCA CGCATTAGTT GCCCCAAAGG CTCCCAGGCA      60

TATGGCTCCT ACTGCTATGC CCTGTTTCAG ATACCACAGA CCTGGTTTGA TGCAGAACTG     120

GCCTGCCAGA AGAGACCTGA AGGACACCTT GTATCTGTGC TCAATGTAGC TGAAGCTTCA     180

TTCTTGGCAT CCATGGTCAA GAACACTGGA AACAGCTACC AATATACCTG GATTGGACTC     240

CATGACCCCA CTCTTGGTGG AGAACCCAAT GGAGGTGGAT GGGAGTGGAG TAACAATGAC     300

ATAATGAATT ATGTCAACTG GGAGAGGAAC CCATCTACTG CCTTAGACCG CGGATTCTGT     360

GGCAGCTTGT CAAGATCTTC TGGATTTCTA AGATGGAGAG ATACCACATG TGAAGTTGAA     420

GTTGCCCTAC GTCTGCAAAT TTACAGGTTA AAATTACCAG ACAGCAAACA GCTT           474

(2) INFORMATION FOR SEQ ID NO:9:

(i) SEQUENCE CHARACTERISTICS:
        (A) LENGTH: 306 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens
        (F) TISSUE TYPE: pancreas (xi) SEQUENCE DESCRIPTION: SEQ ID NO:9:

```
TTTGTTAAGG ATTCCCTTGA GAATTATGTA AAAGTTTTAC AAGAGTCCAT CTCATTCTCT      60

TTGTCCCCCT CAAAGCTGGC TTGCCAGAAG CGGCCCTCTG GAAAACTGGT GTCTGTGCTC     120

AGTGGGGCTG AGGGATCCTT CGTGTCCTCC CTGGTGAGGA GCATTAGTAA CAGCTACTCA     180

TACATCTGGA TTGGGCTCCA TGACCCCACA CAGGTGCGAG TATATCCTCC CCTCTCTGTT     240

ACCTCTCAAG GTACTGTTGT TGCCCAGGCG CACTCCCTGT CCCCAGTCCC TGCCCAGGAA     300

GTACTT                                                               306
```

(2) INFORMATION FOR SEQ ID NO:10:

(i) SEQUENCE CHARACTERISTICS:
        (A) LENGTH: 102 amino acids
        (B) TYPE: amino acid
        (D) TOPOLOGY: unknown (ii) MOLECULE TYPE: protein (vi) ORIGINAL SOURCE:
        (A) ORGANISM: Homo sapiens
        (F) TISSUE TYPE: pancreas (xi) SEQUENCE DESCRIPTION: SEQ ID NO:10:

```
Phe Val Lys Asp Ser Leu Glu Asn Tyr Val Lys Val Leu Gln Glu Ser
 1               5                  10                  15

Ile Ser Phe Ser Leu Ser Pro Ser Lys Leu Ala Cys Gln Lys Arg Pro
            20                  25                  30

Ser Gly Lys Leu Val Ser Val Leu Ser Gly Ala Glu Gly Ser Phe Val
        35                  40                  45

Ser Ser Leu Val Arg Ser Ile Ser Asn Ser Tyr Ser Tyr Ile Trp Ile
    50                  55                  60

Gly Leu His Asp Pro Thr Gln Val Arg Val Tyr Pro Pro Leu Ser Val
65                  70                  75                  80

Thr Ser Gln Gly Thr Val Val Ala Gln Ala His Ser Leu Ser Pro Val
                85                  90                  95

Pro Ala Gln Glu Val Leu
            100
```

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (vi) ORIGINAL SOURCE:
        (A) ORGANISM: Homo sapiens
        (F) TISSUE TYPE: pancreas (xi) SEQUENCE DESCRIPTION: SEQ ID NO:11:

```
         Glu Glu Pro Gln Arg
         1               5

(2) INFORMATION FOR SEQ ID NO:12:

(i) SEQUENCE CHARACTERISTICS:
        (A) LENGTH: 798 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
         (A) ORGANISM: Homo sapiens
         (F) TISSUE TYPE: pancreas (xi) SEQUENCE DESCRIPTION: SEQ ID NO:12:

CGGGAGAGTG ACTCCTGATT GCCTCCTCAA GTCGCAGACA CTATGCTGCC TCCCATGGCC       60

CTGCCCAGTG TATCTTGGAT GCTGCTTTCC TGCCTCATGC TGCTGTCTCA GGTTCAAGGT      120

GAAGAACCCC AGAGGGAACT GCCCTCTGCA CGGATCCGCT GTCCCAAAGG CTCCAAGGCC      180

TATGGCTCCC ACTGCTATGC CTTGTTTTTG TCACCAAAAT CCTGGACAGA TGCAGATCTG      240

GCCTGCCAGA AGCGGCCCTC TGGAAACCTG GTGTCTGTGC TCAGTGGGGC TGAGGGATCC      300

TTCGTGTCCT CCCTGGTGAA GAGCATTGGT AACAGCTACT CATACGTCTG GATTGGGCTC      360

CATGACCCCA CACAGGGCAC CGAGCCCAAT GGAGAAGGTT GGGAGTGGAG TAGCAGTGAT      420

GTGATGAATT ACTTTGCATG GGAGAGAAAT CCCTCCACCA TCTCAAGCCC CGGCCACTGT      480

GCGAGCCTGT CGAGAAGCAC AGCATTTCTG AGGTGGAAAG ATTATAACTG TAATGTGAGG      540

TTACCCTATG TCTGCAAAGT TCACTGACTA GTGCAGGAGG GAAGTCAGCA GCCTGTGTTT      600

GGTGTGCAAC TCATCATGGG CATGAGACCA GTGTGAGGAC TCACCCTGGA AGAGAATATT      660

CGCTTAATTC CCCCAACCTG ACCACCTCAT TCTTATCTTT CTTCTGTTTC TTCCTCCCCG      720

CTAGTCATTT CAGTCTCTTC ATTTTGTCAT ACGGCCTAAG GCTTTAAAGA GCAATAAAAT      780

TTTTAGTCTG CAAAAAAA                                                   798
```

ANTIBODIES SPECIFIC FOR HUMAN PANCREATITIS ASSOCIATED PROTEIN

This is a Division of application Ser. No. 07/778,156 filed on Dec. 19, 1991, now U.S. Pat. No. 5,436,169, which was filed as International Application No. PCT/FR91/00323, on Apr. 18, 1991.

The present invention relates to proteins associated with acute pancreatitis and agents for the diagnosis of this disease.

DESCRIPTION OF THE BACKGROUND

Acute pancreatitis is an inflammatory disease of the pancreas which, pathologically speaking, extends from the simple edematous form to the complete hemorrhagic necrosis of the gland. Necro-hemorrhagic pancreatitis is a very serious disease since, depending on the authors, its mortality is estimated to vary from 30 to 70%. In certain cases it is very difficult to establish the diagnosis of acute pancreatitis with certainty (Sarner, M. et al, Gastroenterol. (1984), 13: 865–870). This diagnosis is based in particular on clinical examination (acute abdominal pain), on the determination of a certain number of substances in the plasma or in the peritoneal fluid (Bradley, J. et al., Br. J. Surg. (1981), 68: 245–246; and Dubick, M. et al., Dig. Dis. Sci. (1987), 32: 305–312). The analytical determinations employed include those for amylase, lipase, trypsin, elastase, ribonuclease, phospholipase A2, α-2 macroglobulin, calcium, LDH, protease inhibitors and others. However, none of them has proved to be specific, practical or above all, discriminating. Hence, it is usually considered sufficient to determine amylasemia. Recently, ultrasonography and computerized tomography have appeared to be able to facilitate the diagnosis of pancreatitis without, however, decisive progress being made (Silverstein, W. et al., Am. J. Roentgenol., (1981), 137: 497–502).

In 1984, Keim et al. published (Digestion, (1984), 29: 242–249) results of the consequences of cannulation of the pancreatic duct and the induction of pancreatitis on the protein composition of the pancreatic juice in the rat, this animal being used an experimental model. After the operation of cannulation (1 to 2 days later), the authors observed a fall in the level of amylase in the pancreatic juice followed, 3 to 4 days after the operation, by a return to the normal amylase level.

Separation of the proteins of the pancreatic juice during this period of remission by means of electrophoresis on polyacrylamide gel (PAGE) showed an additional protein band, detectable as early as 12 hours after the operation and as late as 3 to 4 days after the operation. This protein band did not exist in the untreated control rat. This secretory protein has been called PAP ("pancreatitis-associated protein").

Subsequently, Keim et al. carried out measurements of the amount of PAP present in the pancreatic tissue of the rat, after induction of pancreatitis, by means of tests involving the detection of complement binding.

However, up to now these tests have not made it possible to detect the existence of the PAP in the serum of the rat in which pancreatitis has been induced.

The agents hitherto suggested in the prior art had thus not enabled an adequate identification of the PAP protein in the rat, which raises the question as to the relevance of an investigation in man in order to investigate whether such a protein can be detected.

Furthermore, the results available up to now have not made it possible to estimate the usefulness of PAP for carrying out a diagnosis of pancreatitis.

The inventors have observed that rat polyclonal antibodies which recognize the rat PAP protein do not show significant recognition of a protein in human serum.

Thus, after making this observation, the inventors investigated a more adequate identification of the rat PAP protein, with a view to defining tools of investigation in man: the inventors have now clearly identified the PAP protein in the rat and have determined its amino acid sequence. On the basis of these results, they have developed agents which should make it possible to detect and identify whether a protein corresponding to rat PAP exists in man.

The cloning and sequencing of the PAP messenger RNA starting from a library of rat pancreatic cDNAs has also made it possible to demonstrate unambiguously that the PAP is indeed synthesized by the pancreas. The inventors have also shown that the protein is very weakly expressed in the absence of pancreatic inflammation and strongly expressed during pancreatitis.

In view of the frailty of the patients suffering from pancreatitis, it was out of the question to consider collecting the pancreatic juice from such patients in order to look for the possible presence there of a human PAP protein (PAP-H).

SUMMARY OF THE INVENTION

The inventors have screened a human pancreatic cDNA bank with the aid of a cDNA clone obtained beforehand and corresponding to the rat PAP.

The inventors have succeeded in isolating different clones containing fragments of cDNA capable of hybridizing with the cDNA of the rat PAP, as is described hereafter.

Hence, the present invention relates to cDNA fragments capable of coding for the rat PAP protein as well as to cDNA fragments capable of coding for the proteins of the family of the human PAP. The invention also relates to the proteins encoded by these cDNA fragments.

It also relates to vectors modified by integration of the above-mentioned cDNA fragments, in particular for the expression of these fragments.

The invention also relates to monoclonal or polyclonal antibodies directed against the PAP protein, in particular against the human PAP, as well as to their use in procedures making use of medical imaging, or as agent for the diagnosis of acute pancreatitis in kits and in vitro diagnostic procedures.

BRIEF DESCRIPTION OF THE DRAWINGS

FIG. 1: Expression of the PAP and amylase during experimental acute pancreatitis induced in the rat. Analysis by "Northern blot"—load per lane: 30 fig of total RNA, the same filter was used successively for PAP and amylase. Probes: PAP cDNA (about 800 bp) and amylase (about 1100 bp), labelled with $^{32}P$ with a specific activity of about $2\times10^9$ cpm/mg.

The following phenomena are observed: induction of the expression of the pap gene (12 hours–48 hours) (acute phase); suppression of the induction during recovery—(5–10 days); on the other hand, the amylase falls during the acute phase.

FIG. 2: nucleotide sequence coding for the rat PAP, and the corresponding amino acid sequence (SEQ ID NO: 1 and 2).

FIG. 3: fragment of the nucleotide sequence coding for the human PAP, and the corresponding amino acid sequence (SEQ ID NO: 9 and 10).

FIG. 4: nucleotide sequence (S4) characteristic of the human PAP including the coding sequence S4, and the sequence of amino acids (A3) which corresponds to it (SEQ ID NO: 12 and 7).

DETAILED DESCRIPTION OF THE INVENTION

A first family of DNA fragments according to the invention thus includes the cDNA fragments coding for the rat PAP.

Belonging to this family are cDNA fragments characterized in that they correspond to the following S1 nucleotide sequence (SEQ ID NO:1) coding for the rat PAP protein, to a part or a variant of this sequence in the case in which this part or variant codes for a protein or a peptide recognized by antibodies directed against the rat PAP protein, or which hybridizes with the S1 sequence in a hybridization solution containing 6×SSC, 5×Denhardt, 0.5% SDS, 10 mM EDTA, 200 µg salmon sperm DNA, for 18 hours at 68° C. and after rinsing under the following conditions: 6×SSC, 0.1% SDS, twice for 15 minutes at 65° C.

It is specified that the above abbreviations have the following meanings: 1×SSC=150 mM NaCl, 15 mM sodium citrate; 50×Denhardt=5 g Ficoll, 5 g polyvinylpyrrolidone, 5 g bovine serum albumin in 500 ml of water; SDS: sodium dodecylsulfate; EDTA: sodium ethylene diamine tetraacetate.

Polyclonal antibodies directed against the rat PAP are produced according to standard techniques; such antibodies have been described, for example, by Keim et al. (Clin. Physiol. Biochem., 4: 136–142 (1986)).

A cDNA fragment belonging to the first family of nucleic acids of the invention is also characterized in that it codes for a protein corresponding to one of the following amino acid sequences A1 (SEQ ID NO:2) (amino acid sequence of the protein including the signal peptide) or A2 (SEQ ID NO:3) (amino acid sequence of the mature protein) or for an amino acid sequence having from 40 to 80%, and preferably from 50 to 60% homology with at least one sequence of about 25 amino acids within the A1 (SEQ ID NO:2) or A2 (SEQ ID NO: 3) sequences.

```
Sequence S1:
         10         20         30         40         56         60
    AAAACCATCC AAATCGCCCG CAAGACAGCT AAGGAGGAGC AGAAAGATGA TGAGAGTTAA 70         80         90        100        110        120
    TATGTTGCAT CGCTTGGCCT TCCCAGTCAT GTCCTGGATG CTGCTCTCCT GCCTGATGCT 130        140        150        160        170        180
    CTTATCACAG GTGCAAGGAG AAGACTCTCC GAAGAAAATA CCCTCTGCAC GCATTAGTTG 190        200        210        220        230        240
    CCCCAAAGGC TCCCAGGCAT ATGGCTCCTA CTGCTATGCC CTGTTTCAGA TACCACAGAC 250        260        270        280        290        300
    CTGGTTTGAT GCAGAACTGG CCTGCCAGAA GAGACCTGAA GGACACCTTG TATCTGTGCT 310        320        330        340        350        360
    CAATGTAGCT GAAGCTTCAT TCTTGGCATC CATGGTCAAG AACACTGGAA ACAGCTACCA 370        380        390        400        410        420
    ATATACCTGG ATTGGACTCC ATGACCCCAC TCTTGGTGGA GAACCCAATG GAGGTGGATG 430        440        450        460        470        480
    GGAGTGGAGT AACAATGACA TAATGAATTA TGTCAACTGG GAGAGGAACC CATCTACTGC 490        500        510        520        530        540
    CTTAGACCGC GGATTCTGTG GCAGCTTGTC AAGATCTTCT GGATTTCTAA GATGGAGAGA 550        560        570        580        590        600
    TACCACATGT GAAGTTGAAG TTGCCCTACG TCTGCAAATT TACAGGTTAA AATTACCAGA 610        620        630        640        650        660
    CAGCAAACAG CTTTAGTTTG TCCTGAAGCA CATCCTGTCA AGGGCAAAA TATGAAGACT 670        680        690        700        710        720
    TGCGTAGAAA AAGTGTATTC TATCTACAGT CCATATTGGA GCTCTAATCA TTCTTTAGCC 730        740        750        760        770        780
    AATTTTGTAT AAGTTGTGTC CTCATGTCTT GGAAAGCAGT AATAAACCTC AGTCTCTCTT 790        800        810        820        830        840
    CGAAAAAAAA AAA
```

```
Sequence A1:
MetLeuHisArgLeuAlaPheProValMetSerTrpMetLeuLeuSerCysLeuMetLeuLeuSerGlnValGln GlyGluAspSerProLysLysIleProSerAlaArgIleSerCysProLysGlySerGlnAlaTyrGlySerTyr
```

-continued

CysTyrAlaLeuPheGlnIleProGlnThrTrpPheAspAlaGluLeuAlaCysGlnLysArgProGluGlyHis

LeuValSerValLeuAsnValAlaGluAlaSerPheLeuAlaSerMetValLysAsnThrGlyAsnSerTyrGln

TyrThrTrpIleGlyLeuHisAspProThrLeuGlyGlyGluProAsnGlyGlyGlyTrpGluTrpSerAsnAsn

AspIleMetAsnTyrValAsnTrpGluArgAsnProSerThrAlaLeuAspArgGlyPheCysGlySerLeuSer

ArgSerSerGlyPheLeuArgTrpArgAspThrThrCysGluValGluValAlaLeuArgLeuGlnIleTyrArg

LeuLysLeuPRoAspSerLysGlnLeu

Sequence A2:
    GluAspSerProLysLysIleProSerAlaArgIleSerCysProLysGlySerGlnAlaTyrGlySerTyr CysTyrAlaLeuPheGlnIleProGlnThrTrpPheAspAlaGluLeuAlaCysGlnLysArgProGluGlyHis LeuValSerValLeuAsnValAlaGluAlaSerPheLeuAlaSerMetValLysAsnThrGlyAsnSerTyrGln TyrThrTrpIleGlyLeuHisAspProThrLeuGlyGlyGluProAsnGlyGlyGlyTrpGluTrpSerAsnAsn AspIleMetAsnTyrValAsnTrpGluArgAsnProSerThrAlaLeuAspArgGlyPheCysGlySerLeuSer ArgSerSerGlyPheLeuArgTrpArgAspThrThrCysGluValGluValAlaLeuArgLeuGlnIleTyrArg LeuLysLeuProAspSerLysGlnLeu A second family of DNA fragments according to the invention includes cDNA fragments of a human PAP protein, such as those obtained by the implementation of the following steps:

- an initial screening of a human pancreatic cDNA library, the said human cDNA being inserted into an appropriate cloning vector, comprising the hybridization with probes consisting of the cDNA of the rat PAP protein in a solution constituted by: 6×SSC, 5×Denhardt, 0.5% SDS, 10 mM EDTA, 200 μg of salmon sperm DNA for 18 hours at 68° C., followed by rinsing under the following conditions: 6×SSC, 0.1% SDS, twice for 15 minutes at 65° C.,
- the selection of the positive human cDNA clones which had hybridized during the screening with the cDNA of the rat PAP protein, such clones being called positive,
- a second screening with a cDNA sequence of a PSP protein under the above hybridization conditions with rinsing using 0.1×SSC, 0.1% SDS for 2 hours at 65° C., in order to remove the unspecific clones of human PAP cDNA which had, nonetheless, hybridized with the rat PAP cDNA and
- the recovery of the clones which had not hybridized with the PSP cDNA,
- the recovery of the cDNA fragments from the positive clones obtained.

A particularly useful cloning vector which can be modified by the human cDNA for the construction of the human pancreatic cDNA library is the vector λgt10.

PSP is a protein which exhibits certain structural analogies with the rat PAP. This protein has been described by Giorgi et al., J. Clin. Invest. (1989), 84, 100–106.

The cDNA fragments thus defined are characteristic of the family of proteins which include the human PAP protein.

According to a particular embodiment of the invention, preferred cDNA fragments are those obtained by the implementation of the preceding steps supplemented by the following step, prior to the recovery of the cDNA fragments from the positive clones obtained: screening with the rat PAP cDNA under hybridization conditions such as those described above, with rinsing for 2 hours at 65° C.

According to a useful embodiment of the invention, a cDNA fragment coding for the human PAP corresponds to the following S3 sequence (SEQ ID NO:4):

```
                                            ATG CTG
CCT CCC ATG GCC CTG CCC AGT GTA TCT TGG ATG CTG CTT
TCC TGC CTC ATG CTG CTG TCT CAG GTT CAA GGT GAA GAA
CCC CAG AGG GAA CTG CCC TCT GCA CGG ATC CGC TGT CCC
AAA GGC TCC AAG GCC TAT GGC TCC CAC TGC TAT GCC TTG
TTT TTG TCA CCA AAA TCC TGG ACA GAT GCA GAT CTG GCC
TGC CAG AAG CGG CCC TCT GGA AAC CTG GTG TCT GTG CTC
AGT GGG GCT GAG GGA TCC TTC GTG TCC TCC CTG GTG AAG
AGC ATT GGT AAC AGC TAC TCA TAC GTC TGG ATT GGG CTC
CAT GAC CCC ACA CAG GGC ACC GAG CCC AAT GGA GAA GGT
TGG GAG TGG AGT AGC AGT GAT GTG ATG AAT TAC TTT GCA
TGG GAG AGA AAT CCC TCC ACC ATC TCA AGC CCC GGC CAC
TGT GCG AGC CTG TCG AGA AGC ACA GCA TTT CTG AGG TGG
AAA GAT TAT AAC TGT AAT GTG AGG TTA CCC TAT GTC TGC
AAA GTT CAC
```

The invention also relates to the S4 cDNA fragment (SEQ ID NO:12) which contains the S3 sequence as well as the following DNA sequences (SEQ ID NOS:4–5) corresponding to the $NH_2$ and COOH termini, respectively, of the corresponding protein:

cgggagagtgactcctgattgcctcctcaagtcgcagacact and, tgactagtgcaggagggaagtcagcagcctgtgtttggt
gtgcaactcatcatgggcatgagaccagtgtgaggactcaccctggaagaga
atattcgcttaattcccccaacctgaccacctcattcttatctttcttctgt
ttcttcctcccgctagtcatttcagtctcttcattttgtcatacggcctaa
ggctttaaagagcaataaaatttttagtctgcaaaaaaa According to another embodiment of the invention, the cDNA of the human PAP is characterized in that it codes for the protein corresponding to the following A3 amino acid sequence (SEQ ID NO:7):

Met Leu
Pro Pro Met Ala Leu Pro Ser Val Ser Trp Met Leu Leu
Ser Cys Leu Met Leu Leu Ser Gln Val Gln Gly Glu Glu
Pro Gln Arg Glu Leu Pro Ser Ala Arg Ile Arg Cys Pro
Lys Gly Ser Lys Ala Tyr Gly Ser His Cys Tyr Ala Leu
Phe Leu Ser Pro Lys Ser Trp Thr Asp Ala Asp Leu Ala
Cys Gln Lys Arg Pro Ser Gly Asn Leu Val Ser Val Leu
Ser Gly Ala Glu Gly Ser Phe Val Ser Ser Leu Val Lys
Ser Ile Gly Asn Ser Tyr Ser Tyr Val Trp Ile Gly Leu
His Asp Pro Thr Gln Gly Thr Glu Pro Asn Gly Glu Gly
Trp Glu Trp Ser Ser Ser Asp Val Met Asn Tyr Phe Ala
Trp Glu Arg Asn Pro Ser Thr Ile Ser Ser Pro Gly His
Cys Ala Ser Leu Ser Arg Ser Thr Ala Phe Leu Arg Trp
Lys Asp Tyr Asn Cys Asn Val Arg Leu Pro Tyr Val Cys
Lys Val His

According to another definition of the cDNA fragments of the second family, a cDNA fragment according to the invention is characterized in that it includes a nucleotide sequence exhibiting a homology of at least 60%, and preferably at least 70%, with at least one sequence of about 100 nucleotides comprised in the following S2 sequence (SEQ ID NO:8) which is characteristic of the cDNA of the mature PAP of the rat, or in the S3 sequence given above and characteristic of a cDNA fragment of human PAP.

Sequence S2:
```
          10         20         30         40         50         60
      GAAGACT CTCCGAAGAA AATACCCTCT GCACGCATTA GTTGCCCCAA AGGCTCCCAG 70         80         90        100        110        120
     GCATATGGCT CCTACTGCTA TGCCCTGTTT CAGATACCAC AGACCTGGTT TGATGCAGAA 130        140        150        160        170        180
     CTGGCCTGCC AGAAGAGACC TGAAGGACAC CTTGTATCTG TGCTCAATGT AGCTGAAGCT 190        200        210        220        230        240
     TCATTCTTGG CATCCATGGT CAAGAACACT GGAAACAGCT ACCAATATAC CTGGATTGGA 250        260        270        280        290        300
     CTCCATGACC CCACTCTTGG TGGAGAACCC AATGGAGGTG GATGGGAGTG GAGTAACAAT 310        320        330        340        350        360
     GACATAATGA ATTATGTCAA CTGGGAGAGG AACCCATCTA CTGCCTTAGA CCGCGGATTC 370        380        390        400        410        420
     TGTGGCAGCT TGTCAAGATC TTCTGGATTT CTAAGATGGA GAGATACCAC ATGTGAAGTT 430        440        450        460        470        480
     GAAGTTGCCC TACGTCTGCA AATTTACAGG TTAAAATTAC CAGACAGAA ACAGCTT
```

The invention also relates to cDNA fragments coding for the human PAP which are characterized by their capacity to hybridize with the S1 nucleotide sequence which is characteristic of the cDNA of the rat PAP, and/or with the S2 nucleotide sequence which is characteristic of the cDNA of the mature PAP of the rat, in a hybridization solution containing 6×SSC, 5×Denhardt, 0.5% SDS, 10 mM EDTA, 200 µg of salmon sperm DNA for 18 hours at 68° C., followed by rinsing with a solution consisting of 6×SSC, 0.1% SDS, twice for 15 minutes at 65° C.

A particularly preferred cDNA fragment of the human PAP in the framework of the present application is characterized in that it includes the following nucleotide sequence (SEQ ID NO:9):

```
       10         20         30         40         50         60
TTTGTTAAGC ATTCCCTTTA CAATTATGTA AAAGTTTTAC AAGACTCCAT CTCATTCTCT 70         80         90        100        110        120
TTGTCCCCCT CAAAGCTGGC TTGCCAGAAG CGGCCCTCTG GAAAACTGGT GTCTGTGCTC 130        140        150        160        170        180
AGTGGGGCTG AGGGATCCTT CGTGTCCTCC CTGGTGAGGA GCATTAGTAA CAGCTACTCA 190        200        210        220        230        240
TACATCTGGA TTGGGCTCCA TGACCCCACA CAGGTGCGAG TATATCCTCC CCTCTCTGTT 250        260        270        280        290        300
ACCTCTCAAG GTACTGTTGT TGCCCAGGCG CACTCCCTGT CCCCAGTCCC TGCCCAGGAA

GTACTT
```

The inventors have observed that the protein sequence deduced from this human nucleotide sequence exhibits certain homologies with the sequence coding for the rat PAP protein, although the only evidence up to now obtained from antibodies directed against the rat PAP did not enable the human PAP protein to be detected in a given biological sample.

The identification of a cDNA fragment coding for the human PAP protein now makes it possible to contemplate the production of this protein, in particular by means of genetic engineering, as well as the production of antibodies which can be used as diagnostic agents of acute pancreatitis.

The invention also relates to a nucleic acid fragment characterized in that it is a DNA fragment complementary to the cDNA fragments defined above, or also in that it is the RNA fragment corresponding to these cDNAs.

The invention also relates to any fragment of a nucleotide sequence coding for the human PAP which is capable of being used as a probe, after suitable labelling of the said fragment, for the purpose of developing a means to detect the nucleic acid characteristic of the human PAP in a biological sample.

The invention also relates to the human PAP protein as obtained by the expression of a cDNA fragment of the human PAP, such as that defined above, by means of a suitable system of expression, for example a cell host transformed by an expression vector, itself modified by the insertion of the above-mentioned cDNA fragment of the human PAP.

A special human PAP protein according to the invention is a protein such as that produced by the expression of a cDNA fragment of the human PAP, inserted in phase in a pEX vector, in E.coli, in particular in the E.coli strain pop2136.

Human PAP proteins according to the invention are also characterized in that their amino acid sequences exhibit a homology of at least 50%, and preferably at least 60% and in the most preferred case at least 70% of at least one sequence of about 25 amino acids included in the A2 sequence of the mature PAP protein of the rat, or in the A3 sequence of the human PAP protein described above.

According to a particular embodiment of the invention, the human PAP protein corresponds to the A3 sequence given on the preceding pages.

The invention also relates to any fragment of the A3 sequence provided that it is recognized by antibodies recognizing this sequence, in particular monoclonal antibodies directed specifically against the A3 sequence.

The human PAP protein may be produced by the procedures of genetic engineering or also by purification, for example by means of chromatography, starting from a biological sample containing it.

According to a particular specification of the invention, the human PAP protein corresponding to the foregoing specifications, comprises the following amino acid sequence (SEQ ID NO:10):

```
                                                                 39
Phe Val Lys Asp Ser Leu Glu Asn Tyr Val Lys Val Leu   13

78
Gln Glu Ser Ile Ser Phe Ser Leu Ser Pro Ser Lys Leu   26

117
Ala Cys Gln Lys Arg Pro Ser Gly Lys Leu Val Ser Val   39

156
Leu Ser Gly Ala Glu Gly Ser Phe Val Ser Ser Leu Val   52

195
Arg Ser Ile Ser Asn Ser Tyr Ser Tyr Ile Trp Ile Gly   65

234
Leu His Asp Pro Thr Gln Val Arg Val Tyr Pro Pro Leu   78

273
Ser Val Thr Ser Gln Gly Thr Val Val Ala Gln Ala His   91

306
Ser Leu Ser Pro Val Pro Ala Gln Glu Val Leu           102
```

Also included in the framework of the present invention is the rat PAP protein characterized in that it corresponds to the A2 amino acid sequence (SEQ ID NO:3) shown above, or to a variant or a part of this sequence provided that this part or this variant is recognized by antibodies directed against the rat PAP protein or in that it exhibits a homology of at least 50%, and preferably at least 60% with the above A2 sequence (SEQ ID NO:3) of rat PAP, or with the A3 sequence (SEQ ID NO:7) of the human PAP.

The invention also relates to the rat PAP protein corresponding to the A1 sequence (SEQ ID NO:2) or to a variant of A1 exhibiting the characteristics defined above with respect to the A2 amino acid sequence (SEQ ID NO:3).

In the rat the PAP is present in very low amounts in the normal pancreas, and its synthesis may be considerably increased in the event of acute pancreatitis to a level about 50 to 100 times higher than that which prevails in the normal pancreas.

The level of the rat PAP protein undergoes an increase in the pancreatic juice at the time of acute pancreatitis whereas the levels of the other enzymes diminish.

Furthermore, in pancreatitis all of the pancreatic secretory proteins escape into the blood. Consequently, the attempt to determine in the blood or in another biological sample of a human patient (for example urine or peritoneal fluid) the PAP protein whose synthesis is considerably increased in the event of pancreatitis, suggests that the normal/pathological differential will be much greater than that found in the tests usually used for detection, and hence it will be much easier to detect.

With this objective, the invention also relates to antibodies characterized in that they recognize the human PAP protein previously defined, and these antibodies may be either polyclonal or monoclonal.

Monoclonal antibodies are, for example, antibodies such as those produced by a hybridoma formed beforehand by fusion of a myeloma cell with a spleen cell of an animal previously immunized with a human PAP protein.

The invention also relates to the hybridomas formed by fusion of myeloma cells and spleen cells of an animal previously immunized with the human PAP protein, in particular with the protein corresponding to the A3 amino acid sequence.

Particularly useful monoclonal antibodies in the framework of the invention are those which recognize specifically the NH$_2$-terminal portion of the human PAP. Particularly useful antibodies are further defined in that they recognize the human PAP and in that they show no immunological reaction with the other lectins.

As an example, a valuable monoclonal antibody, in particular for the detection of the human PAP (SEQ ID NO:11), is a monoclonal antibody directed against the following peptide of the human PAP: Glu Glu Pro Gln Arg (SEQ ID NO:11). In order to monitor this peptide in detection tests for the human PAP, a tyrosine residue has been added to the arginine, for example, so as to make labelling with iodine possible according to the usual labelling procedures.

The invention also relates to anti-idiotypic antibodies directed against the antigenic determinants of the antibodies of the invention which recognize the human PAP.

Other antibodies according to the invention are monoclonal antibodies which recognize the rat PAP protein.

A protocol for the immunization of selected animals, in particular mice and rabbits, for the implementation of the invention is the protocol described by Kohler and Milstein, Nature (1975), 256, 495–497.

Also included in the framework of the invention is an expression and/or cloning vector, characterized in that it comprises a DNA fragment selected from the previously defined fragments.

Particularly useful expression and/or cloning vectors for the implementation of the invention include the expression plasmid pEX which is capable of expressing the cDNA of the human PAP protein in a bacterium, for example E.coli.

Other vectors are selected as a function of the host in which they are to be expressed. In this respect, a vector of the baculovirus type may be used in the case of mammalian cells.

The invention also relates to a cell host transformed by an expression vector such as that previously defined under conditions leading to the production of the protein or peptide encoded by the DNA fragment of the invention, inserted in this vector.

As an example, cell hosts constituting a suitable expression system for the DNA fragments of the invention are bacteria such as E.coli, in particular the strain pop2136.

The invention also relates to the expression product of the cell host transformed in the manner just described.

Advantageously, the choice as to whether the DNA fragment according to the invention is expressed in a prokaryotic or eukaryotic host should be made as a function of the product desired, particularly in respect to its glycosylation.

As examples, useful cell hosts for the implementation of the invention are bacteria, for example E.coli, yeasts, insect or mammalian cells, for example CHO cells.

The present invention also relates to compositions, characterized in that they contain at least one antibody selected from those which have been previously defined, directed against the human PAP protein. Such a composition may be a composition for in vitro diagnosis, to be used on a biological sample such as blood, urine or the peritoneal fluid of a patient showing the symptoms of acute pancreatitis.

Where appropriate, the antibodies used will be labelled by suitable chemical markers.

The invention also relates to a kit for the in vitro diagnosis of acute pancreatitis in a defined biological sample, characterized in that it contains:

at least one antibody selected from those previously described which are capable of detecting the presence of an antigen of the human PAP type in the said biological sample, the said antibodies being labelled, depending on the type of labelling, a reagent to detect the presence of a complex of a specific antigen-antibody type, a negative control.

Preferably, the antibodies used are specific for the human PAP if they show no reaction with the other known lectins.

In order to carry out the labelling of the antibodies according to the invention, recourse may be had for example to radioisotopes, to chemical or enzymatic markers, and to chemiluminescent markers.

Moreover, the invention relates to a procedure for the in vitro detection of acute pancreatitis starting from a biological sample and which comprises the following steps:

placing of the biological sample likely to contain the human PAP in contact with antibodies directed against the human PAP, detection of the antigen-antibody reaction between the above-mentioned antibodies and the human PAP.

The invention also relates, where appropriate, to the use of the antibodies directed against the PAP in the form of a composition containing several labelled antibodies for visualization by medical imaging of the pancreas, the antibody being labelled beforehand by means of a radioisotope or a chemical or enzymatic marker. The visualization may permit the detection of the presence of human PAP.

In this connection, the invention relates to an observation procedure of the pancreas characterized by:

the injection of a composition mentioned above into a patient under physiologically acceptable conditions, the observation of a reaction between the antibodies contained in the above-mentioned composition and the human PAP if it is present.

Other characteristics and advantages of the invention will become apparent in the examples and the figures as described above:

1. Construction of a Rat Pancreatic cDNA Library in the Vector λgt11

Preparation of rat pancreatic RNA: the preparation was carried out by following exactly the procedure of Chirgwin, J. M. et al., Biochemistry (WASH) (1979), 19, 5294–5299. The messenger RNA fraction of this total RNA was separated by chromatography on a column of oligo-dT cellulose according to the technique of Aviv, H. and Leder, P., Proc. Natl. Acad. Sci., USA, (1972), 69, 1408–1412.

Preparation of the cDNA: the pancreatic cDNA was synthesized with the aid of the kit marketed by Amersham France S. A. (code RPN 1256), by following exactly the directions of the manufacturer.

Construction of the library: the library was constructed in the expression vector λgt11 with the aid of the kit marketed by Amersham France S. A. (code RPN 1280), by following exactly the directions of the manufacturer.

2. Construction of a Human Pancreatic cDNA Library in the Vector λgt10

Preparation of human pancreatic RNA and synthesis of the cDNA corresponding to the RNA messengers: fragments of normal pancreas obtained from organ donors who have undergone brain death were treated as described above for the rat pancreas.

Construction of the library: the library was constructed in the cloning vector λgt10 with the aid of the kit marketed by Amersham France S. A. (code RPN 1257), by following the directions of the manufacturer.

3. Screening of the Human Pancreatic cDNA Library with a Clone Expressing the Rat PAP Starting from the rat pancreatic cDNA library constructed according to the above method, a clone recognized by polyclonal antibodies directed against the rat PAP was selected.

The cDNA of this clone of rat PAP was isolated and used as a probe to screen the human pancreatic cDNA bank obtained in λgt10, as described above.

In the first stage, the screening was carried out under the following conditions of stringency: 6×SSC, 5×Denhardt, 0.5% SDS, 10 mM EDTA, 200 µg of salmon sperm DNA for 18 hours at 68° C., following by rinsing with 6×SSC, 0.1% SDS, twice for 15 minutes at 65° C. This procedure made it possible to obtain about 80 clones of human cDNA.

Subsequently a screening with the PSP cDNA was carried out for the purpose of removing the clones which were not characteristic of the human PAP but which were, nonetheless, capable of hybridizing with the cDNA of the rat PAP under the above conditions: about 50 clones were recovered which thus contained a cDNA fragment coding for a protein or a polypeptide belonging to the family of the human PAP protein.

From these clones those were selected whose cDNA exhibits a very strong homology with the rat PAP protein, by performing a second screening using the cDNA of rat PAP under the following conditions of stringency: 6×SSC, 5×Denhardt, 0.5% SDS, 10 mM EDTA, 200 µg of salmon sperm DNA for 18 hours at 68° C., followed by rinsing with 6×SSC, 0.1% SDS for 2 hours at 65° C. 9 positive clones were selected in this way.

4. Sequencing of the Selected Clones

The inserts of the useful clones were subcloned in the phages M13mp18–M13mp19 as described in "Molecular Cloning, a laboratory manual", Sambrook, J. Fritsch, E. F., and Maniatis T. eds., Cold Spring Harbor Laboratory Press (1990). The sequencing of the recombinant M13 phages was performed by means of the procedure described by Sanger F. et al., Proc. NAtl. Acad. Sci. (USA) (1977), 74, 5463–5467, by using the universal primer marketed by Amersham (code N4511).

5. Expression of a Fragment of PAP in *E.coli* with the Aid of the Expression Plasmid pEX and Preparation of Antibodies against the Hybrid Protein An expression kit employing the plasmid pEX in *E. coli*, marketed by the Genofit company under the catalogue number G2104, was used by following the directions of the manufacturer. Restriction fragments corresponding to the sequence coding for the protein were inserted into the pEX plasmid. The recombinant plasmids served to transform bacteria (*E.coli* strain pop2136). The proteins of the recombinant bacteria were analysed by means of electrophoresis on a 7.5% polyacrylamide gel. The protein band corresponding to the hybrid PAP was excised, homogenised in Freund's adjuvant and injected into rabbits at a rate of 3 injections per rabbit at intervals of 3 weeks, each injection containing about 20 µg of hybrid protein. The blood of the rabbits was then collected and the G immunoglobulins were purified on a column of protein A-SEPHAROSE (Pharmacia-France).

We claim:

1. An antibody specific for human pancreatitis associated protein of SEQ ID NO. 7 (PAP), wherein said antibody binds said human PAP in human serum.

2. The antibody of claim 1, which is a monoclonal antibody.

3. The antibody of claim 1, which is a polyclonal antibody.

4. A hybridoma which produces the antibody of claim 1, wherein the hybridoma is produced by a process comprising fusing a myeloma cell with a spleen cell of an animal previously immunized with human pancreatitis associated protein (PAP) of SEQ ID NO:7.

5. A composition comprising at least one antibody of claim 1 and a carrier.

6. The composition according to claim 6, wherein at least one antibody is labeled.

7. A kit, comprising:
   at least one antibody according to claim 1.

8. The kit of claim 7, wherein at least one antibody is labeled.

9. A polyclonal antibody specific for human pancreatitis associated protein of SEQ ID NO. 7 (PAP), obtained by immunization of an animal with said human PAP.

10. An antibody which specifically binds the sequence Glu Glu Pro Gln Arg (SEQ ID NO: 11).

11. A monoclonal antibody specific for human pancreatitis associated protein of SEQ ID NO. 7 (PAP), wherein said monoclonal antibody is produced by a hybridoma obtained by fusion of a myeloma cell with a spleen cell of an animal previously immunized with human PAP.

12. A method of producing an antibody specific for human pancreatitis associated protein (PAP) comprising immunizing an animal with isolated human PAP of SEQ ID NO. 7.

13. A method of assaying for the presence of human PAP protein in a biological sample, comprising:
   contacting the sample with the antibody of claim 1; and
   assaying for the formation of an antibody-PAP complex.

14. A method of detecting human PAP in vivo, comprising:
   administering the antibody of claim 1 to a human patient; and
   assaying for the formation of an antibody-PAP complex.

* * * * *